(12) United States Patent
Inukai et al.

(10) Patent No.: US 6,527,725 B1
(45) Date of Patent: *Mar. 4, 2003

(54) BLOOD PRESSURE ESTIMATING APPARATUS

(75) Inventors: Hidekatsu Inukai, Komaki (JP); Akihiro Yokozeki, Nagoya (JP); Keizoh Kawaguchi, Komaki (JP); Kiyoyuki Narimatsu, Komaki (JP)

(73) Assignee: Colin Corporation, Komaki (JP)

( * ) Notice: Subject to any disclaimer, the term of this patent is extended or adjusted under 35 U.S.C. 154(b) by 74 days.

This patent is subject to a terminal disclaimer.

(21) Appl. No.: 09/768,265

(22) Filed: Jan. 25, 2001

(51) Int. Cl.[7] .................................................. A61B 5/00
(52) U.S. Cl. ........................ 600/485; 600/494; 600/500
(58) Field of Search .................................. 600/500, 485, 600/490, 493–6

(56) References Cited

U.S. PATENT DOCUMENTS

| | | | |
|---|---|---|---|
| 5,131,391 A | | 7/1992 | Sakai et al. |
| 5,752,920 A | * | 5/1998 | Ogura .......................... 600/494 |
| 6,027,453 A | * | 2/2000 | Inukai et al. ................. 600/494 |
| 6,027,455 A | * | 2/2000 | Inukai et al. ................. 600/494 |
| 6,036,651 A | * | 3/2000 | Inukai et al. ................. 600/485 |
| 6,036,652 A | | 3/2000 | Inukai et al. |
| 6,186,953 B1 | * | 2/2001 | Narimatsu et al. ........... 600/490 |

FOREIGN PATENT DOCUMENTS

| | | |
|---|---|---|
| JP | 7-9305 | 2/1995 |
| JP | 7-308295 | 11/1995 |

* cited by examiner

Primary Examiner—Robert L. Nasser
(74) Attorney, Agent, or Firm—Oliff & Berridge, PLC

(57) ABSTRACT

An apparatus for estimating a blood pressure of a living subject, including a measuring device which iteratively measures a blood pressure of the subject, a first device for obtaining first information relating to velocity of propagation of pulse wave, a second device for obtaining at least one of second information relating to heart rate and third information relating to area defined by volume pulse wave, a memory which stores groups of information each group of which includes the blood pressure, the first information, and at least one of the second information and the third information, a determining device for determining an expression representing a relationship between (A) blood pressure, and (B1) first information and (B2) at least one of (B21) second information and (B22) third information, and having a first coefficient for the first information, at least one second coefficient for at least one of the second and third information, and a constant, the determining device determining the coefficients and constant of the expression by applying a multiple regression analysis to more than a predetermined number of groups of information last stored in the memory, the predetermined number being equal to a total number of the coefficients and the constant, and an estimating device for successively estimating, according to the expression, a blood pressure of the subject based on each first information and at least one of each second information and each third information.

13 Claims, 8 Drawing Sheets

FIG. 5

| BLOCK-PRESSURE RANGES (mmHg)<br>COEFFICIENTS | ~40 | ~80 | ~120 | ~160 | ~200 | 200~ |
|---|---|---|---|---|---|---|
| $\alpha$ | $\alpha 1$ | $\alpha 2$ | $\alpha 3$ | $\alpha 4$ | $\alpha 5$ | $\alpha 6$ |
| $\beta$ | $\beta 1$ | $\beta 2$ | $\beta 3$ | $\beta 4$ | $\beta 5$ | $\beta 6$ |
| $\gamma$ | $\gamma 1$ | $\gamma 2$ | $\gamma 3$ | $\gamma 4$ | $\gamma 5$ | $\gamma 6$ |

$(\alpha > 0, \beta, \gamma < 0)$

BLOOD PRESSURE ESTIMATING APPARATUS

BACKGROUND OF THE INVENTION

1. Field of the Invention

The present invention relates to a blood pressure estimating apparatus for successively estimating an intraarterial blood pressure of a living subject, based on information non-invasively obtained from the circulatory organ of the subject.

2. Related Art Statement

There is known, as a blood pressure (BP) measuring apparatus for non-invasively measuring an intraarterial blood pressure of a living subject, a so-called Korotokoff-sound-type BP measuring apparatus or oscillometric-type BP measuring apparatus. The Korotokoff-sound-type BP measuring apparatus automatically determines a blood pressure of the subject, based on a pressing pressure of a pressing band being wound around a body portion of the subject at the time of change of Korotokoff sounds produced by changing the pressing pressure of the pressing band. The oscillometric-type BP measuring apparatus automatically determines a blood pressure of the subject, based on the variation of amplitude of pulse wave produced by changing the pressing pressure of the pressing band.

In an operating room, an intensive care unit, or the like, it may be needed to measure successively a blood pressure of a patient because an urgent medical treatment or cure may be needed. In the case, however, where the conventional BP measuring apparatus is used, it takes several tens of seconds from the start of blood pressure measurement to obtain a blood pressure of the patient. If an interval between successive blood pressure measurements is shortened to obtain a blood pressure at a short period, congestion may occur to the body portion of the patient due to the increased frequency of pressing of the pressing band, whereby errors may occur to the measured blood pressure values.

Meanwhile, there has been proposed a BP estimating apparatus including means for determining a velocity of propagation of a pulse wave which propagates through an artery of a living subject, and means for successively estimating, according to a predetermined relationship between blood pressure and velocity of propagation of pulse wave, an intraarterial blood pressure of the subject, based on the determined velocity of propagation of the pulse wave. An example of the BP estimating apparatus is disclosed in Laid-open Publication No. 7-9305 of unexamined Japanese Utility Model Application and Laid-open Publication No. 7-308295 of unexamined Japanese Patent Application.

However, the above BP estimating apparatus has only the function of estimating successively a blood pressure based on a propagation time of a pulse wave or a propagation velocity of a pulse wave. In the case where the blood pressure is estimated based on only the pulse-wave propagation time or the pulse-wave propagation velocity, the estimated blood pressure can not enjoy high accuracy. Therefore, it is needed to frequently calibrate the BP estimating apparatus, based on an actual blood pressure measured by the Korotokoff-sound-type BP measuring apparatus or the oscillometric-type BP measuring apparatus.

SUMMERY OF THE INVENTION

It is therefore an object of the present invention to provide a blood pressure estimating apparatus which estimates, with high accuracy, a blood pressure of a living subject.

The above object has been achieved by the present invention. According to a first feature of the present invention, there is provided an apparatus for successively estimating an intraarterial blood pressure of a living subject, based on information non-invasively obtained from a circulatory organ of the subject, comprising a blood-pressure measuring device which includes an inflatable cuff adapted to apply a pressing force to a body portion of the subject and iteratively measures, by changing the pressing force of the cuff, a blood pressure of the subject at a predetermined period; a first means for non-invasively obtaining, from the circulatory organ of the subject, a set of first information which relates to a velocity of propagation of a pulse wave which propagates through an artery of the subject, at least each time the blood-pressure measuring device measures a blood pressure of the subject; a second means for non-invasively obtaining, from the circulatory organ of the subject, at least one of a set of second information which relates to a heart rate of the subject and a set of third information which relates to an area defined by a volume pulse wave from a peripheral portion of the subject, at least each time the blood-pressure measuring device measures the blood pressure; a first memory device which stores a plurality of groups of information each group of which comprises the blood pressure measured by the blood-pressure measuring device, the set of first information obtained by the first means when the blood pressure is measured by the blood-pressure measuring device, and the at least one of the set of second information and the set of third information obtained by the second means when the blood pressure is measured by the blood-pressure measuring device; an expression determining means for determining an expression representing a relationship between (A) blood pressure, and (B1) first information and (B2) at least one of (B21) second information and (B22) third information, the expression having a first coefficient for the first information, at least one second coefficient for the at least one of the second information and the third information, and a constant, the expression determining means determining the first and second coefficients and the constant of the expression by applying a multiple regression analysis to more than a first predetermined number of the groups of information last stored in the first memory device, the first predetermined number being equal to a total number of the first coefficient, the at least one second coefficient, and the -constant; and a blood-pressure estimating means for successively estimating, according to the determined expression representing the relationship between (A) blood pressure, and (B1) first information and (B2) at least one of (B21) second information and (B22) third information, an intraarterial blood pressure of the subject, based on each of a plurality of sets of first information successively obtained by the first means and at least one of each of a plurality of sets of second information, and each of a plurality of sets of third information, successively obtained by the second means when the each of sets of first information is obtained by the first means.

In the present BP estimating apparatus, the BP estimating means successively estimates, according to the expression representing the relationship between (A) blood pressure, and (B1) first information and (B2) at least one of (B21) second information and (B22) third information, an intraarterial blood pressure of the subject, based on each set of first information successively obtained by the first means and each set of second and/or third information successively obtained by the second means. Therefore, as compared with the case where a blood pressure is estimated based on only the first information, the present apparatus estimates the intraarterial blood pressure, based on, in addition to the first information, at least one of the second information as a parameter on the side of the heart of the subject that changes in relation with the blood pressure and the third information as a parameter on the side of peripheral portion of the subject that changes in relation with the blood pressure. Accordingly, the accuracy of the estimated blood pressure is improved.

In addition, the first memory device stores, at the predetermined period, a group of information comprising a blood pressure measured by the blood-pressure measuring device, a set of first information obtained by the first means when the blood pressure is measured by the blood-pressure measuring device, and at least one of a set of second information and a set of third information obtained by the second means when the blood pressure is measured by the blood-pressure measuring device, and the expression determining means determines the first and second coefficients and the constant of the expression by applying a multiple regression analysis to more than a first predetermined number of groups of information last stored in the first memory device, the first predetermined number being equal to a total number of the first and second coefficients and the constant. The first predetermined number is counted retrospectively from the last group of information that are last stored in the first memory device. Thus, any dispersion included in the groups of information stored in the first memory device can be well removed, and the expression or the relationship can be so determined as to be suitable for the individual subject. Here, it is noted that the first information and the second and/or third information obtained when the blood pressure is measured by the BP measuring device may change because of the change of physical condition of the subject, such as respiration or arrhythmia, or the occurrence of artifact noise. That is, the groups of information stored in the first memory device may include the dispersion which does not result from the change of blood pressure of the subject. In contrast, if the expression or the relationship is determined based on only the first predetermined number of groups of information stored in the first memory device, the determined expression or relationship is influenced by the dispersion of the groups of information that does not result from the change of blood pressure of the subject.

According to a second feature of the present invention, the expression determining means comprises means for determining the first and second coefficients and the constant of the expression by applying the multiple regression analysis to not more than a second predetermined number of the groups of information last stored in the first memory device, the second predetermined number being greater than the first predetermined number. The first predetermined number may be three or four, and the second predetermined number may be from 10 to 20, preferably 20.

The second predetermined number corresponds to a time duration (e.g., 60 minutes) in which, it can be expected, a relationship between the BP values measured by the BP measuring device and the sets of first information obtained by the first means does not change basically. That is, in a short duration, the BP values and the sets of first information keeps a good correlation; but, in a long duration, this correlation gradually decreases because of the change of physical condition of the subject (e.g., a patient), such as the condition of circulatory organ. Therefore, if the expression or the relationship is determined based on the groups of information which include one or more groups of information which were stored in the first memory device, an excessively long time before, the determined expression or relationship may not be suitable for the current physical condition of the subject.

According to a third feature of the present invention, the second means obtains the set of second information and the set of third information, and the blood-pressure estimating means comprises means for estimating, according to the expression representing the relationship between (A) blood pressure, and (B1) first information, (B21) second information, and (B22) third information, the intraarterial blood pressure of the subject, based on the each set of first information obtained by the first means, and each set of second information and each set of third information obtained by the second means when the each set of first information is obtained by the first means. In this case, it is not needed to frequently calibrate the estimating apparatus, based on an actual blood pressure of the subject measured by using the cuff, because the estimated blood pressure enjoys higher accuracy in comparison with an estimated blood pressure which is estimated based on only the first information.

According to a fourth feature of the present invention, the first means comprises means for obtaining, as the set of first information, a time, DT, which is needed for the pulse wave to propagate between two different portions of the artery, the second means comprises means for obtaining, as the set of second information, a heart-beat period, RR, of the subject, and means for obtaining, as the set of third information, a ratio, VR, of the area of the volume pulse wave to the heart-beat period RR, and the blood-pressure estimating means comprises means for successively estimating, according to the expression representing the relationship between (A) blood pressure, EBP, and (B1) time DT, (B21) period RR, and (B22) ratio VR, defined as follows: $EBP=\alpha(1/DT)+\beta RR+\gamma VR+\delta$, where $\alpha$ is the first coefficient, $\beta$ and $\gamma$ are the second coefficients, and $\delta$ is the constant, an intraarterial blood pressure of the subject, based on each of a plurality of values of the time DT successively obtained by the first means, and each of a plurality of values of the period RR, and each of a plurality of values of the ratio VR, successively obtained by the second means when the each value of the time DT is obtained by the first means. The two different portions of the artery may comprise the heart and the capillaries of the subject. In the present apparatus, the BP estimating means estimates the intraarterial blood pressure based on the second information as the parameter on the side of the heart of the subject and the third information as the parameter on the side of the peripheral portion of the subject as well as the first information. In this case, it is not needed to frequently calibrate the present apparatus, based on an actual blood pressure of the subject measured by using the cuff, because the estimated blood pressure enjoys higher accuracy in comparison with an estimated blood pressure which is estimated based on only the first information.

According to a fifth feature of the present invention, the estimating apparatus further comprises a second memory device which stores at least one group of predetermined first and second coefficients $\alpha$, $\beta$, $\gamma$ for the expression that are predetermined by applying the multiple regression analysis to a plurality of groups of information which are obtained from a plurality of persons and each group of which comprises a blood pressure obtained from a corresponding one of the persons, and a time DT, a period RR, and a ratio VR which are obtained from the one person when the blood pressure is obtained from the one person, and, before the first memory device stores more than the first predetermined number of groups of information, the blood pressure estimating means successively estimates, according to the expression having the one group of predetermined first and second coefficients α, β, γ, an intraarterial blood pressure of the subject, based on each of a plurality of values of the time DT successively obtained by the first means and each of a plurality of values of the period RR, and each of a plurality of values of the ratio VR, successively obtained by the second means when the each value of the time DT is obtained by the first means. In this case, the present estimating apparatus can obtain, even in an early period of operation thereof, a widely applicable expression or relationship with which the apparatus can successively estimate a blood pressure of the subject with accuracy.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which:

FIG. 5 is a view for explaining a plurality of groups of predetermined coefficients, α, β, γ, for an expression (2) that correspond to a plurality of blood-pressure ranges, respectively;

DETAILED DESCRIPTION OF PREFERRED EMBODIMENTS

Figure 1:
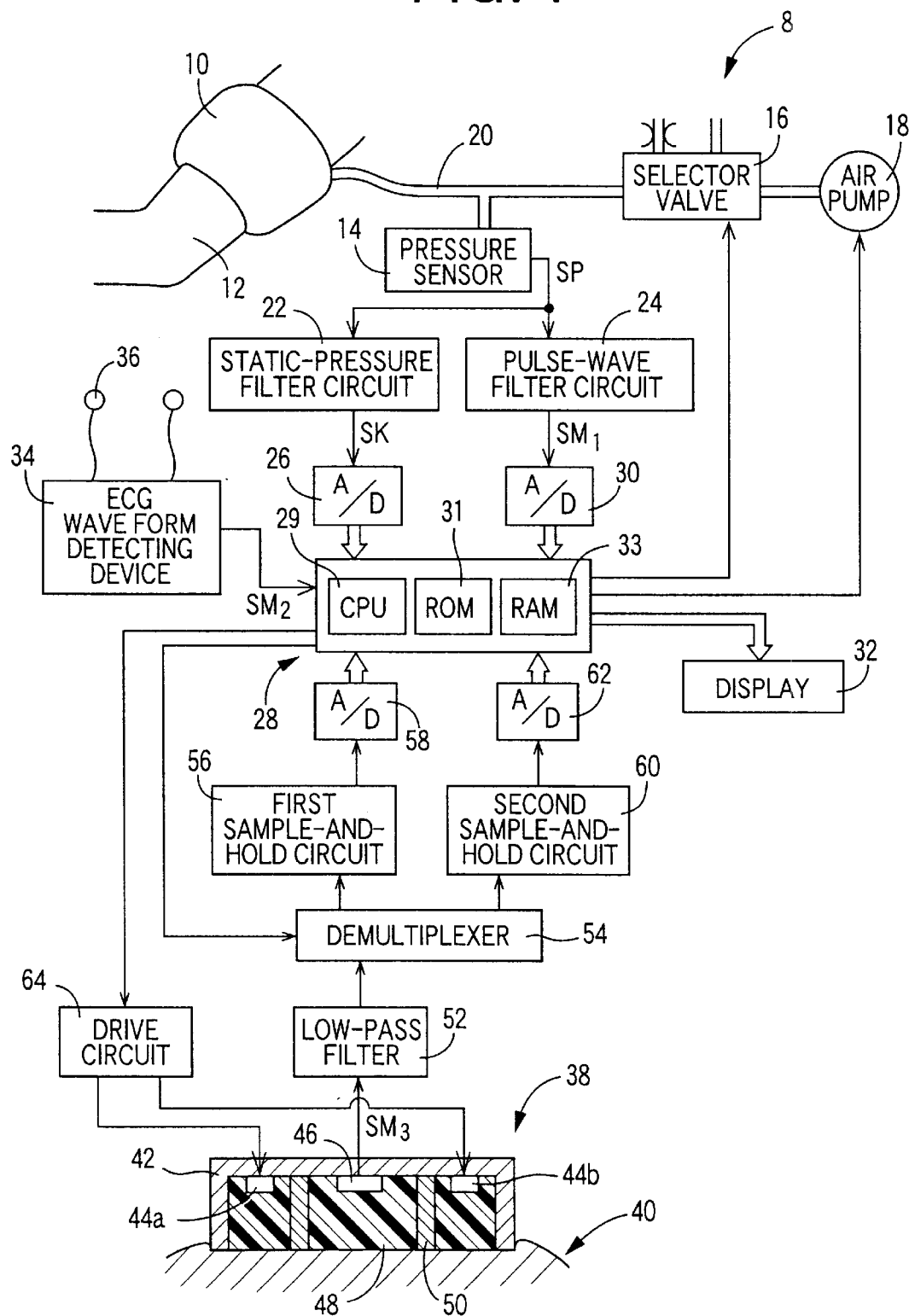
FIG. 1 is a diagrammatic view of a blood pressure estimating apparatus 8 embodying the present invention.

Referring first to FIG. 1, there will be described a blood pressure (BP) estimating apparatus 8 embodying the present invention.

As shown in FIG. 1, the BP estimating apparatus 8 includes a cuff 10 which has a belt-like cloth bag and a rubber bag accommodated in the cloth bag and which is adapted to be wound around an upper arm 12 of a patient, a pressure sensor 14, a selector valve 16, and an air pump 18 each of which is connected to the cuff 10 via a piping 20. The selector valve 16 is selectively placed in an inflation position in which the selector valve 16 permits a pressurized air to be supplied from the air pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representing the detected pressure, to each of a static-pressure filter circuit 22 and a pulse-wave filter circuit 24. The static-pressure filter circuit 22 includes a low-pass filter and extracts, from the pressure signal SP, a static-pressure component contained in the signal SP, i.e., a cuff-pressure signal SK representing the static pressure in the cuff 10. The cuff-pressure signal SK is supplied to a control device 28 via an analog-to-digital (A/D) converter 26. The pulse-wave filter circuit 24 includes a band-pass filter and extracts, from the pressure signal SP, an oscillating component having predetermined frequencies, i.e., a pulse-wave signal SM1. The pulse-wave signal SM1 is supplied to the control device 28 via an A/D converter 30. The pulse-wave signal SM1 represents a pulse wave, i.e., an oscillatory pressure wave which is produced from a brachial artery (not shown) of the patient in synchronism with the heartbeat of the patient and is propagated to the cuff 10.

The control device 28 is provided by a so-called microcomputer including a central processing unit (CPU) 29, a read only memory (ROM) 31, a random access memory (RAM) 33 and an input-and-output (I/O) port (not shown). The CPU 29 processes signals according to the control programs pre-stored in the ROM 31 by utilizing the temporary-storage function of the RAM 33, and supplies drive signals to the selector valve 16 and the air pump 18 through the I/O port.

The BP estimating apparatus 8 further includes an electrocardiographic (ECG) waveform detecting device 34 which continuously detects an ECG waveform representing an action potential of cardiac muscle of a living subject, through a plurality of electrodes 36 being put on predetermined portions of the subject, and supplies an ECG-waveform signal SM2 representing the detected ECG waveform, to the control device 28. The ECG-waveform detecting device 34 is used for detecting a Q-wave or an R-wave of the ECG waveform that corresponds to a time point when the output of blood from the heart of the subject toward the aorta is started.

The BP estimating apparatus 8 still further includes a photoelectric-pulse-wave detecting probe 38 (hereinafter, referred to as the "probe") which is employed as part of a pulse oximeter. The probe 38 functions as a peripheral-pulse-wave detecting device for detecting a peripheral pulse wave propagated to a peripheral artery including capillaries. The probe 38 is adapted to be set on a skin or a body surface 40 of the subject, e.g., an end portion of a finger of the subject, with the help of a band (not shown) such that the probe 38 closely contacts the body surface 40. The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second group of light emitting elements 44a, 44b need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shade member 50 which is disposed between the light emitting elements 44 and the light receiving element 46, for preventing the lights emitted toward the body surface 40 by the light emitting elements 44 and directly reflected from the body surface 40, from being received by the light receiving element 46.

The first and second groups of light emitting elements 44a, 44b emit a red light having about 660 nm wavelength and an infrared light having about 800 nm wavelength, respectively. The first and second light emitting elements 44a, 44b alternately emit the red and infrared lights at a predetermined frequency. The lights emitted toward the body surface 40 by the light emitting elements 44 are reflected from a body tissue of the subject where a dense capillaries occur, and the reflected lights are received by the common light receiving element 46. In place of the 660 nm and 800 nm wavelengths lights, the first and second light emitting elements 44a, 44b may emit various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is well reflected by both of the two sorts of hemoglobin.

The light receiving element 46 outputs, through a low-pass filter 52, a photoelectric-pulse-wave signal SM3 representing the received or detected amount of light. The light receiving element 46 is connected to the low-pass filter 52 via an amplifier or the like. The low-pass filter 52 removes, from the photoelectric pulse-wave signal SM3 input thereto, noise having frequencies higher than that of the pulse wave, and outputs the noise-free signal SM3, to a demultiplexer 54. The photoelectric pulse wave represented by the photoelectric-pulse-wave signal SM3 can be said as a volume pulse wave which is produced in synchronism with the pulse of the subject. That is, the photoelectric pulse wave is a pulse-synchronous wave.

The demultiplexer 54 is alternately switched according to signals supplied thereto from the control device 28 in synchronism with the light emissions of the first and second light emitting elements 44a, 44b. Thus, the demultiplexer 54 successively supplies, to the I/O port (not shown) of the control device 28, an electric signal $SM_R$ representing the red light through a first sample-and-hold circuit 56 and an A/D converter 58, and an electric signal $SM_{IR}$ representing the infrared light through a second sample-and-hold circuit 60 and an A/D converter 62. The first and second sample-and-hold circuits 56, 60 hold the electric signals $SM_R$, $SM_{IR}$ input thereto, respectively, and do not output those electric signals to the A/D converters 58, 62, before the prior signals $SM_R$, $SM_{IR}$ are completely converted by the two A/D converters 58, 62, respectively.

In the control device 28, the CPU 29 carries out a BP measuring operation according to the control programs pre-stored in the ROM 31 by utilizing the temporary-storage function of the RAM 33. More specifically described, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined duration. In synchronism with the alternate light emissions by the first and second light emitting elements 44a, 44b, the CPU 29 generates a switch signal SC to the demultiplexer 54 so as to correspondingly place the demultiplexer 54 in a first or a second position. Thus, the signals $SM_R$, $SM_{IR}$ are separated from each other by the demultiplexer 54 such that the signal $SM_R$ is supplied to the first sample-and-hold circuit 56 while the signal $SM_{IR}$ is supplied to the second sample-and-hold circuit 60. Further, the CPU 29 determines a degree of oxygen saturation in the blood of the subject, based on respective amplitudes of the signals $SM_R$, $SM_{IR}$, according to a predetermined expression pre-stored in the ROM 31. The blood oxygen saturation determining method is disclosed in U.S. Pat. No. 5,131,391.

The BP estimating apparatus 8 further includes a display 32 which is connected to the control device 28. The CPU 29 of the control device 28 supplies electric signals to the display 32. The display 32 includes a CRT (cathode ray tube) and a speaker.

Figure 2:
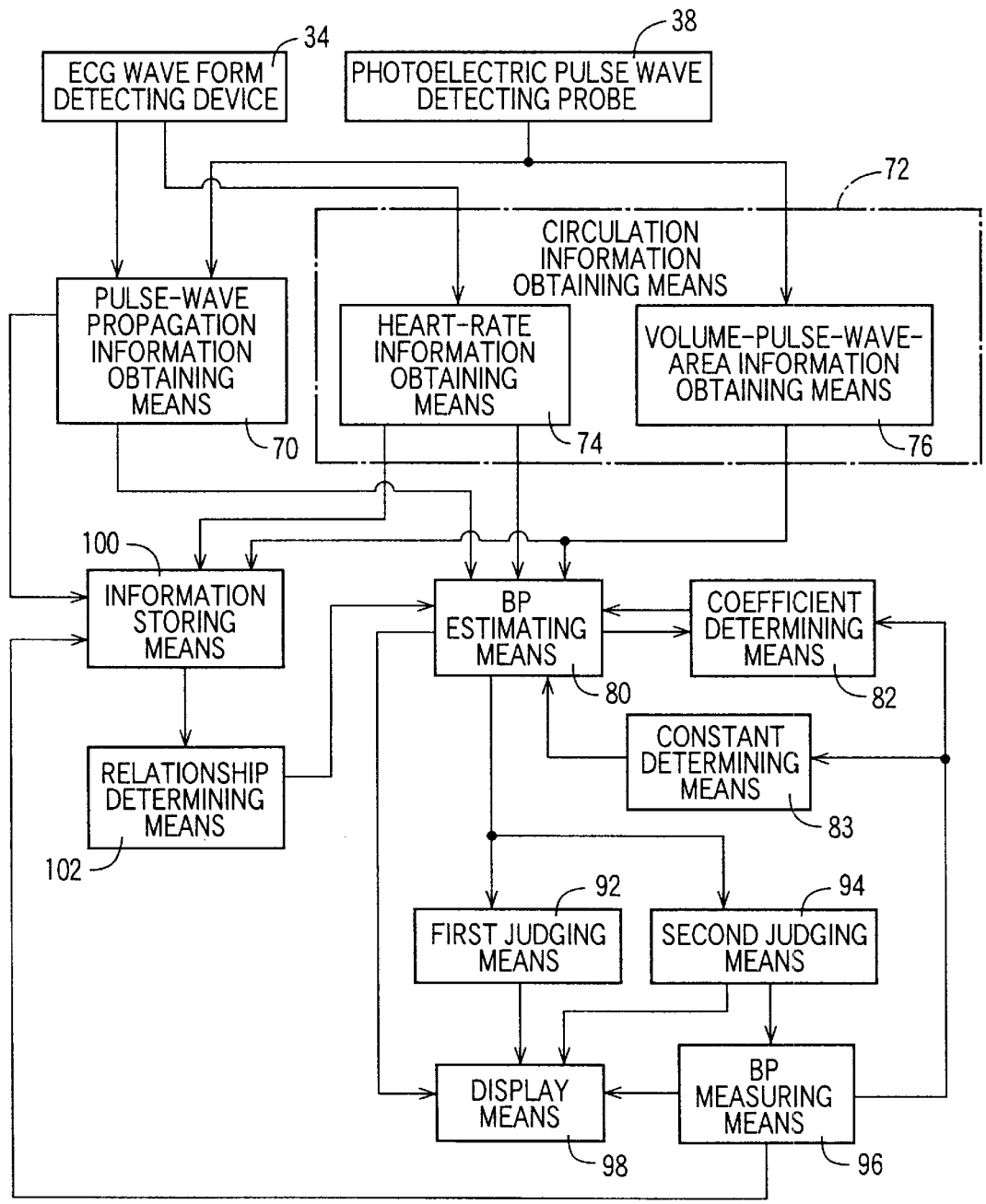
FIG. 2 is a block diagram for illustrating essential functions of a control device 28 of the apparatus of FIG. 1.
Figure 3:
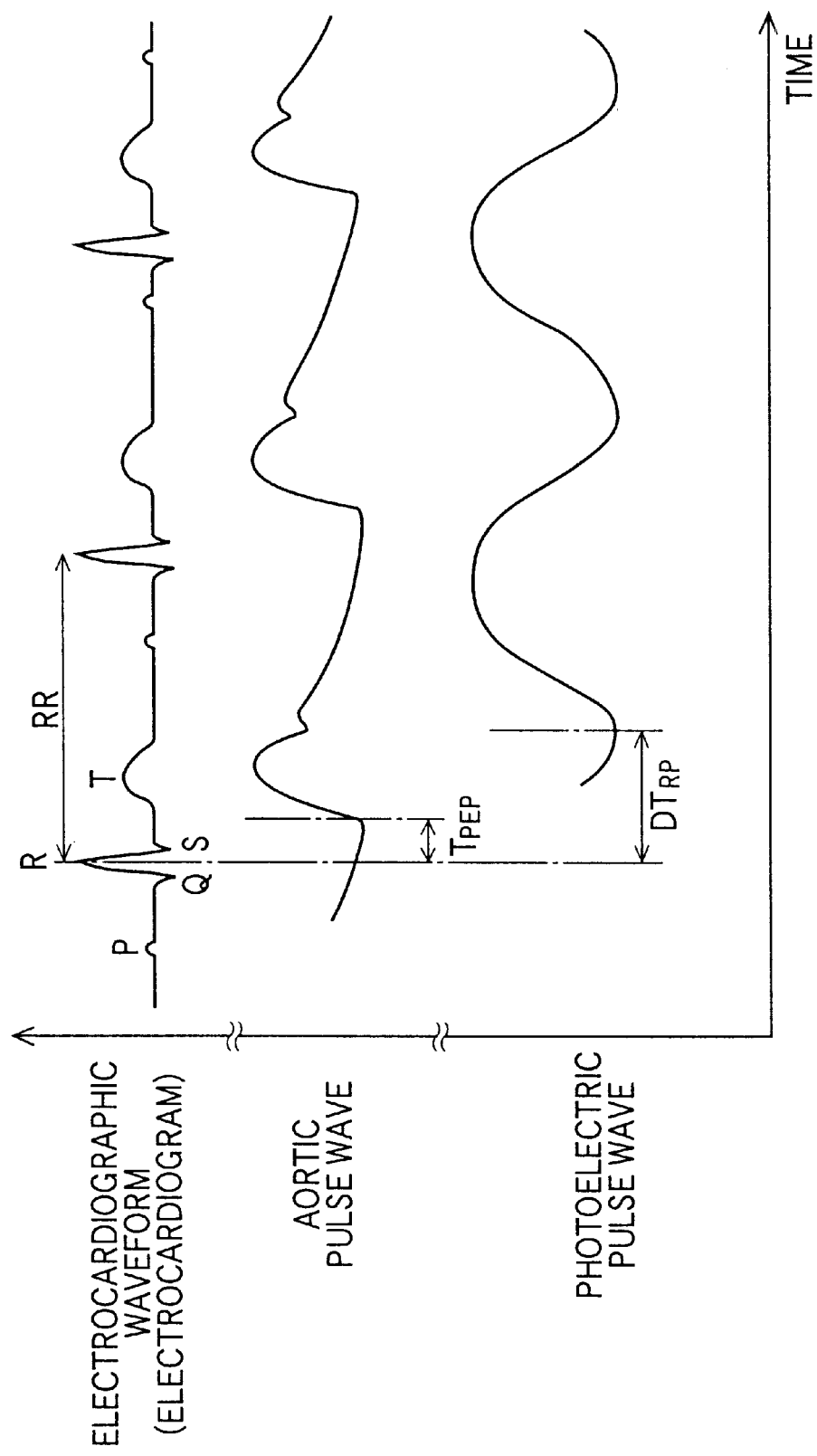
FIG. 3 is a view for explaining a time difference, $DT_{RP}$, obtained by the operation of the control device 28.

FIG. 2 illustrates essential functions of the control device 28 of the present BP estimating apparatus 8. In the figure, a pulse-wave-propagation (PWP) information obtaining means 70 obtains information which relates to a velocity $V_M$ of propagation of a pulse wave which propagates through an artery, such as a time duration $DT_{RP}$ which is needed for the pulse wave to propagate between two different portions of the artery. The PWP information obtaining means 70 includes a time difference calculating means for calculating, as a pulse-wave-propagation (PWP) time $DT_{RP}$, a time difference between a predetermined point (e.g., an R-wave) of the ECG waveform of each of periodic pulses successively detected by the ECG waveform detecting device 34 and a predetermined point (e.g., a start point, that is, a minimum point) of the waveform of a corresponding one of periodic pulses of the photoelectric (volume) pulse wave detected by the probe 38, as shown in FIG. 3. The PWP information obtaining means 70 calculates a velocity $V_M$ (m/sec) of the pulse wave propagating through the artery of the subject, based on the calculated time $DT_{RP}$, according to the following expression (1) pre-stored in the ROM 31:

$$V_M = L/(DT_{RP} - T_{PEP}) \qquad (1)$$

where

L (m) is a length of the artery as measured from the left ventricle via the aorta to the position at which the probe 38 is set; and $T_{PEP}$ (sec) is a pre-ejection period between the R-wave of ECG waveform of each pulse and the minimum point of the waveform of a corresponding pulse of an aortic pulse wave. The values L and $T_{PEP}$ are constants, and are experimentally obtained in advance.

Figure 4:
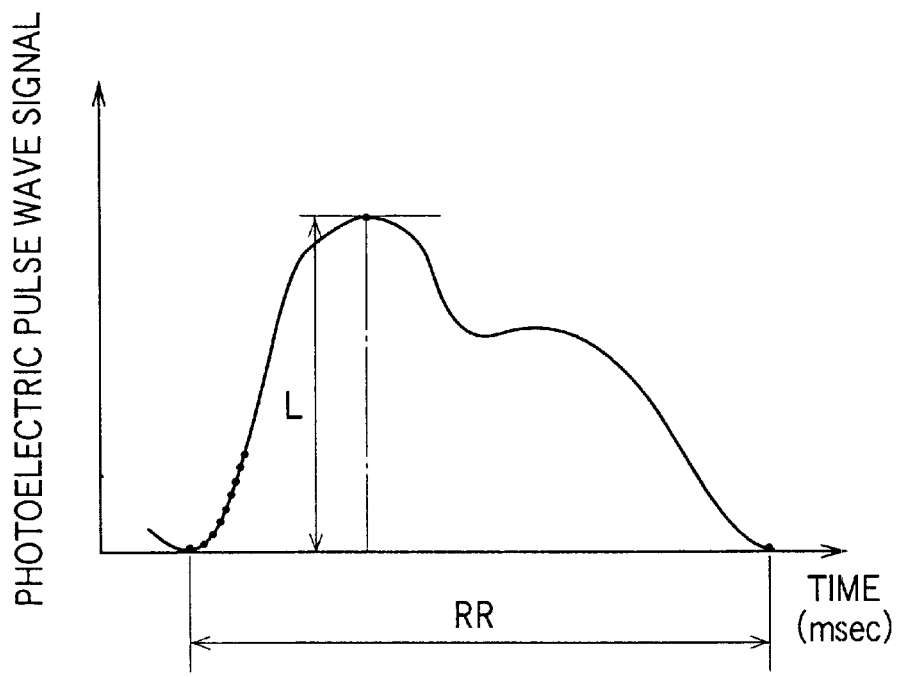
FIG. 4 is a view for explaining a volume-pulse-wave area, VP.

A circulation-information obtaining means 72 includes at least one of a heart-rate (HR) information obtaining means 74 and a volume-pulse-wave-area (VPWA) information obtaining means 76. The HR information obtaining means 74 obtains information which relates to a heart rate of a living subject, such as a heart rate HR, a heart-beat period RR, a pulse rate, a pulse period, or the like. The VPWA information obtaining means 76 obtains information which relates to an area defined by a volume pulse wave from a peripheral portion of the subject. As shown in FIG. 4, an area VP is defined by the waveform of each heartbeat-synchronous pulse of the photoelectric (volume) pulse wave detected by the probe 38, and is normalized based on a heart-beat period RR and an amplitude L of the pulse. The waveform of each pulse of the photoelectric pulse wave is defined by a series of data points indicative of respective magnitudes which are input at a predetermined interval such as several milliseconds to several tens of milliseconds. The area VP is obtained by integrating, in the heart-beat period RR, the respective magnitudes of each pulse being input at the predetermined interval, and then a normalized pulse-wave area NVP is obtained by calculating the following expression: NVP=VP/(RR×L). The volume-pulse-wave area information may be the area VP, a ratio VR of the area VP to the heart-beat period RR, a ratio VR' of a product of the area VP and the amplitude L of the photoelectric pulse wave to the heart-beat period RR, and a ratio of the area VP to a product of the heart-beat period RR and the amplitude L, that is, the normalized pulse-wave area NVP. Both of the heart rate information and the volume-pulse-wave area information change in relation with the intraarterial blood pressure of the subject. That is, the change of blood pressure occurs due to the change of cardiac output on the proximal side of the subject and the change of peripheral vascular resistance on the distal side of the subject. The heart rate information reflects the amount of cardiac output while the volume-pulse-wave area information reflects the magnitude of peripheral vascular resistance.

A BP estimating means 80 calculates, according to an expression representing a relationship between blood pressure, and pulse-wave-propagation information and at least one of heart-rate information and volume-pulse-wave-area information, an estimated blood pressure of the subject, based on the obtained pulse-wave-propagation information, and at least one of the obtained heart-rate information and the obtained volume-pulse-wave-area information. For example, the blood pressure estimating means 80 calculates an estimated blood pressure EBP of the subject, based on a time $DT_{RP}$ obtained by the PWP information obtaining means 70, a period RR obtained by the HR information obtaining means 74, and a ratio VR obtained by the VPWA information obtaining means 76, according to the following expression (2):

$$EBP = \alpha(1/DT_{RP}) + \beta RR + \gamma VR + \delta \quad (2)$$

where $\alpha$, $\beta$, $\gamma$ are coefficients and $\delta$ is a constant.

The expression (2) represents a relationship between blood pressure of the subject, and time $DT_{RP}$, period RR, and ratio VR of the subject.

A coefficient determining means 82 selects, from a plurality of groups of predetermined coefficients ($\alpha$, $\beta$, $\gamma$) which respectively correspond to a plurality of blood-pressure ranges, one group of predetermined coefficients which corresponds to a reference value of the blood pressure of the subject, so that an estimated blood pressure EBP of the subject is calculated according to the expression (2) including the selected group of predetermined coefficients. The plurality of groups of predetermined coefficients are pre-stored in the ROM 31. For example, in the case where an actual systolic blood pressure value $BP_{SYS}$ measured using the cuff 10 by a BP measuring means 96 (which will be described below) is employed as a reference value of the blood pressure of the subject, the coefficients determining means 82 selects, from the pre-stored plurality of groups of predetermined coefficients which respectively correspond to the plurality of blood-pressure ranges, one group of predetermined coefficients which corresponds to the measured systolic blood pressure value $BP_{SYS}$. In this case, the BP estimating means 80 successively calculates an estimated systolic blood pressure value $EBP_{SYS}$ of the subject. In place of the systolic blood pressure value $BP_{SYS}$, a diastolic blood pressure value $BP_{DIA}$ or a mean blood pressure value $BP_{MEAN}$ may be employed as a reference value of the blood pressure of the subject. When one group of predetermined coefficients which corresponds to the reference diastolic blood pressure value $BP_{DIA}$ is selected, the BP estimating means 80 calculates an estimated diastolic blood pressure $EBP_{DIA}$. When one group of predetermined coefficients which corresponds to the reference mean blood pressure value $BP_{MEAN}$ is selected, the BP estimating means 80 calculates an estimated mean blood pressure value $EBP_{MEAN}$.

A constant determining means 83 determines the constant $\delta$ of the expression (2) used by the BP estimating means 80, by subtracting, from the actual blood pressure value of the subject which has been measured using the cuff 10 and has been used by the coefficient determining means 82 to select the one group of predetermined coefficients $\alpha$, $\beta$, $\gamma$, the sum of the first product of the coefficient $\alpha$ and the inverse of a time $DT_{RP}$, and at least one of the second product of the coefficient $\beta$ and a period RR, and the third product of the coefficient $\gamma$ and a ratio VR. The time $DT_{RP}$, the period RR, and the ratio VR are ones which have been obtained when the actual blood pressure value is measured using the cuff 10.

FIG. 5 illustrates a plurality of groups of predetermined coefficients which respectively correspond to a plurality of blood-pressure ranges. In the figure, six groups of predetermined coefficients ($\alpha$, $\beta$, $\gamma$) correspond to six blood pressure ranges each defined by 40 mmHg. Usually, if the blood pressure of the subject increases, the inverse ($1/DT_{RP}$) of time difference $DT_{RP}$ tends to increase, and the period RR and the ratio VR tend to decrease. Accordingly, in FIG. 5, the coefficient $\alpha$ is a positive value, and the coefficients $\beta$, $\gamma$ are negative values. The plurality of groups of predetermined coefficients are pre-stored in the ROM 31. Each of the plurality of groups of coefficients ($\alpha$, $\beta$, $\gamma$) are determined by applying a multiple regression analysis to many sets of information obtained from many persons. Each of the sets of information includes a blood pressure value measured using a cuff, or the like, from a corresponding one of the persons, and a time $DT_{RP}$, a period RR, and a ratio VR obtained from the same person when the blood pressure is measured from the person. For example, best unbiased estimate values of the coefficients and constant $\alpha$, $\beta$, $\gamma$, $\delta$ of the expression (2), for each blood-pressure range, are obtained by applying the least square method to at least four sets of information each of which includes three explanatory variables (independent variables), i.e., a time $DT_{RP}$, a period RR, and a ratio VR, and one objective variable (dependent variable), i.e., an estimated blood pressure EBP corresponding to the each blood-pressure range. The thus obtained unbiased estimate values of $\alpha$, $\beta$, $\gamma$ are pre-stored in the ROM 31.

Figure 8:
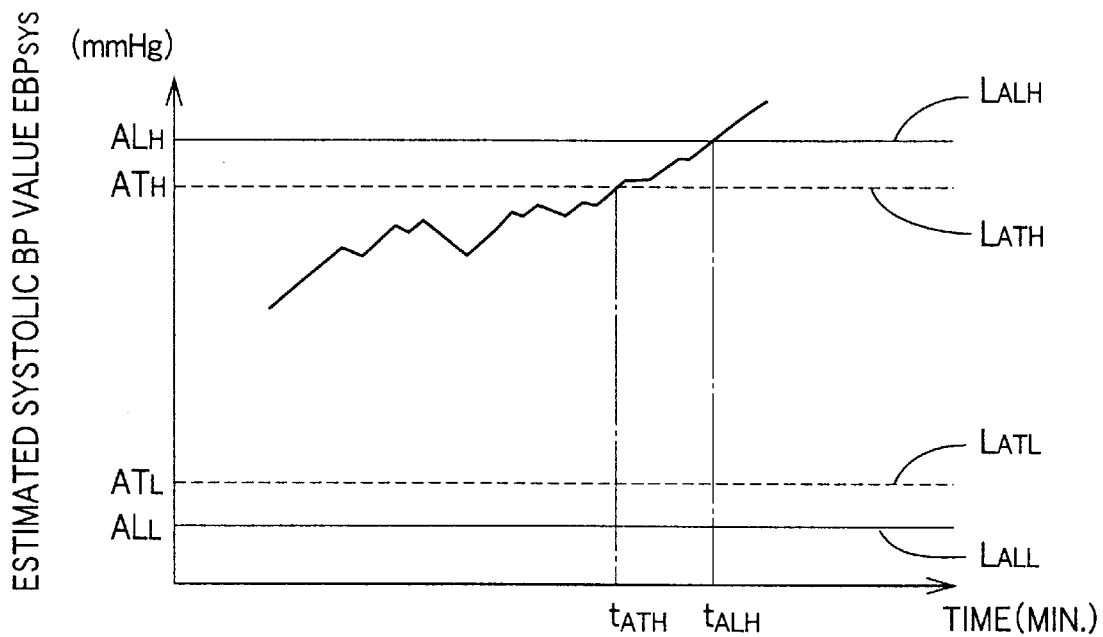
FIG. 8 is a graph showing a trend graph of estimated blood pressure values, EBP, that are displayed by a display device 32.

A first judging means 92 judges whether or not a physical parameter which is obtained from the subject and which changes in relation with the blood pressure of the subject falls within a first reference range ($AL_L$–$AL_H$, FIG. 8). The first judging means 92 functions as an alarm judging means. The physical parameter is selected from the blood-pressure-relating information which changes in relation with the blood pressure of the subject, the heart-rate information which relates to the heart rate which changes to adjust the blood pressure on the proximal side of the subject, and the volume-pulse-wave area information which reflects the peripheral vascular resistance which changes to adjust the blood pressure on the distal side of the subject. The first reference range ($AL_L$–$AL_H$) is defined by a critical range in which the blood pressure of the subject indicates a need for an emergency medical treatment. The first reference range ($AL_L$–$AL_H$) may be a constant range of the parameter, or a predetermined range of the amount or rate of change of the current value of the parameter from the prior value of the same obtained when the last blood pressure value is measured using the cuff 10.

A second judging means 94 judges whether or not the physical parameter falls within a second reference range ($AT_L$–$AT_H$) which is fully contained in the first reference range ($AL_L$–$AL_H$). The second judging means 94 functions as an alert judging means. For example, an upper limit $AT_H$ of the second reference range is determined at a value lower, by a predetermined value or percentage, than the upper limit $AL_H$ of the first reference range. A lower limit $AT_L$ of the second reference range is determined at a value higher, by a predetermined value or percentage, than the lower limit $AL_L$ of the first reference range.

A BP measuring means 96 automatically measures a blood pressure of the subject, based on variation of respective amplitudes of heartbeat-synchronous pulses of the pulse wave produced by changing the pressing pressure of the cuff 10, at a predetermined calibration period, or when the second judging means 94 makes a negative judgment that the physical parameter does not fall within the second reference range. For example, the BP measuring means 96 measures a systolic, a mean and a diastolic blood pressure value $BP_{SYS}$, $BP_{MEAN}$, $BP_{DIA}$ of the subject, according to a well-known oscillometric method, based on variation of respective amplitudes of pulses of the pulse wave represented by the pulse-wave signal SM1 obtained while the pressing pressure of the cuff 10 which has been quickly increased to a target value PCM (e.g., 180 mmHg), is slowly decreased from the target value PCM, at the rate of about 3 mmHg/sec.

A display means 98 displays, in a two-dimensional coordinate system defined by a first axis indicative of time and a second axis indicative of physical parameter (or rate of change of the parameter), successively obtained data indicative of the physical parameter (or the rate of change thereof) along the first axis. Moreover, the display means 98 displays two first lines $L_{ALH}$, $L_{ALL}$ (indicated at solid lines in FIG. 8) which are indicative of the upper and lower limits of the first reference range, respectively, and which are parallel to the first axis, and two second lines $L_{ATH}$, $L_{ATL}$ (indicated at broken lines in FIG. 8) which are indicative of the upper and lower limits of the second reference range, respectively, and which are parallel to the first axis. Further, the display means 98 outputs a visible or audible message indicating that the physical parameter does not fall within the first or second reference range.

An information storing means 100 stores, in a predetermined area (not shown) of the RAM 33, a group of information including the BP value BP measured by the BP measuring means 96, the pulse-wave-propagation (PWP) information obtained by the PWP information obtaining means 70 when the BP value BP is measured by the BP measuring means 96, i.e., immediately before or after the cuff 10 presses the upper arm 12 of the subject, or while the cuff 10 is pressing the arm 12, and at least one of the heart-rate (HR) information and the volume-pulse-wave-area (VPWA) information obtained by the circulation-information obtaining means 72 when the BP value BP is measured by the BP measuring means 96.

A relationship (or expression) determining means 102 determines a relationship between blood pressure BP, and PWP information and at least one of HR information and VPWA information. More specifically described, the relationship determining means 102 determines an expression representing the relationship, the expression having a first coefficient for the PWP information, at least one second coefficient for at least one of the HR information and the VPWA information, and a constant. The relationship or expression determining means 102 determines the first and second coefficients and the constant of the expression by applying a multiple regression analysis (i.e., a kind of statistical analysis) to more than a first predetermined number of groups of information which have been last stored in the first memory device, the first predetermined number being equal to a total number of the first coefficient, the at least one second coefficient, and the constant. The thus determined may be the above-described expression (2): $EBP = \alpha(1/DT_{RP}) + \beta RR + \gamma VR + \delta$, where $DT_{RP}$ is the PWP time, RR is the heartbeat period, VR is the VPWA ratio, the $\alpha$ is the first coefficient, $\beta$, $\gamma$ are the second coefficients, and $\delta$ is the constant.

The reason why the relationship determining means 102 uses more than the first predetermined number of groups of information that is equal to the total number of the first and second coefficients and the constant, is as follows: In the case where the BP estimating means 80 estimates a BP values of the subject according to the above-indicated expression (2), the expression (2) has the three coefficients and the single constant. Therefore, the relationship determining means 102 uses more than 4 (i.e., not less than 5) groups of information which have been last stored in the RAM 33, and determines the coefficients and constant $\alpha$, $\beta$, $\gamma$, $\delta$ of the expression (2) by applying the multiple regression analysis to the 5 or more last groups of information. Since the three coefficients $\alpha$, $\beta$, $\gamma$ and the single constant $\delta$ are unknown, those four unknowns can be determined based on four groups of information stored in the RAM 33. However, those groups of information, each comprising the PWP time $DT_{RP}$, the heartbeat period RR, and the VPWA ratio VR, include dispersion produced by some causes different than the change of blood pressure of the subject; such as the change of physical condition of the subject, for example, respiration or arrhythmia, and the occurrence of artifact noise. Therefore, if the coefficients $\alpha$, $\beta$, $\gamma$ and the constant $\delta$ of the expression (2) are determined based on only the four groups of information last stored in the RAM 33, the thus determined coefficients and constant may be adversely influenced by the dispersion which is introduced into the groups of information, independent of the change of blood pressure of the subject. However, this dispersion is not statistically biased with respect to the true relationship between blood pressure BP, and PWP time $DT_{RP}$, heartbeat period RR and VPWA ratio VR. Therefore, this dispersion can be reduced by using more than 5 groups of information last stored in the RAM 33, in determining the expression (2) or the relationship.

Meanwhile, the expression or relationship determining means 102 determines the coefficients and constant of the expression by applying the multiple regression analysis to not more than a second predetermined number of groups of information which have been last stored in the first memory device, the second predetermined (i.e., upper limit) number being greater than the first predetermined (i.e., lower limit) number. The second number may be from 10 to 20, preferably 20 corresponding to about 60 minutes. It is speculated that within this time duration (i.e., about 60 minutes), the relationship (e.g., the coefficient $\alpha$) between the blood pressure BP and the PWP information is kept substantially constant, and as many as possible groups of information that have been stored in the RAM 33 within this time duration are used to determine the coefficients and constant of the expression (2). In a short duration, the BP values BP, and the sets of PWP information obtained when those BP values are measured, respectively, keep a good correlation; but, in a long duration, this correlation gradually decreases. If the expression is determined based on the groups of information that include one or more groups of information which had been stored in the first memory device, an excessively long time before, the thus determined expression may not be suitable for the current condition of the subject.

Next, there will be described the operation of the control device 28 of the BP estimating apparatus 8 by reference to the flow charts of FIGS. 6 and 7.

Figure 6:
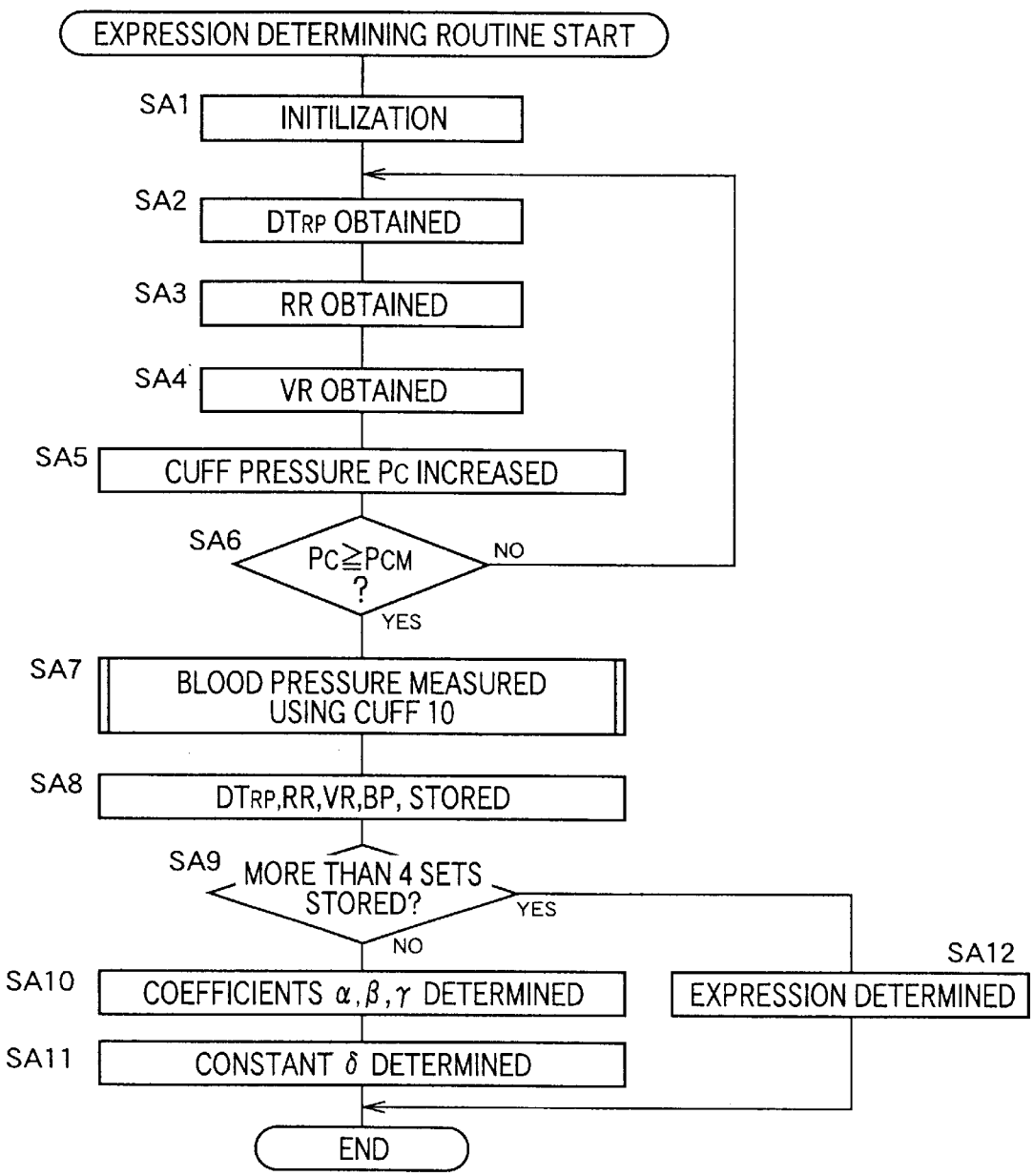
FIG. 6 is a flow chart representing an expression determining routine according to which the apparatus of FIG. 1 is operated.

The control of the CPU 29 begins with Step SA1 of the expression determining routine of FIG. 6, where flags, counters and registers (not shown) are reset. Step SA1 is followed by Step SA2. At Step SA2, the CPU 29 judges whether or not an R-wave of the ECG waveform of one pulse and a waveform of a corresponding pulse of the photoelectric pulse wave have been read in and, if a positive judgment is made, the CPU 29 calculates, as a pulse-wave propagation time $DT_{RP}$, a time difference between the R-wave of the ECG waveform of the pulse and the minimum point of the waveform of the corresponding pulse of the photoelectric pulse wave. Step SA2 corresponds to the PWP information obtaining means 70.

Step SA2 is followed by Step SA3 to measure, as a heart-beat period RR (sec), a time difference between the R-wave of the ECG waveform of the pulse read in Step SA2 of the current control cycle and the R-wave of the ECG of the pulse read in the prior control cycle. Step SA3 corresponds to the HR information obtaining means 74. Step SA3 is followed by Step SA4 to obtain a ratio VR (=VP/RR) of an area VP defined by the pulse of the photoelectric pulse wave read in at Step SA2, to the heart-beat period RR measured at Step SA3. Step SA4 corresponds to the VPWA information obtaining means 76. Steps SA3 and SA4 correspond to the circulation information obtaining means 72.

Next, the CPU 29 carries out Steps SA5, SA6, and SA7 corresponding to the BP measuring means 96. At Step SA5, the CPU 29 controls the selector valve 16 to its inflation position and controls the air pump 18 to start, thereby quickly increasing the cuff pressure $P_C$. At Step SA6, the CPU 29 judges whether the cuff pressure $P_C$ is equal to, or higher than, a predetermined target value $P_{CM}$ (e.g., 180 mmHg). If a negative judgement is made at Step SA6, Steps SA5 and SA6 are repeated to increase the cuff pressure $P_C$ until a positive judgement is made at Step SA6.

Meanwhile, if a positive judgement is made at Step SA6, the control of the CPU 29 goes to Step SA7 to stop the air pump 18 and switch the selector valve 16 to its slow-deflation position, so as to slowly decrease the cuff pressure $P_C$ at a predetermined rate of about 3 mmHg/sec. The CPU 29 determines a systolic blood pressure value $BP_{SYS}$, a mean blood pressure value $BP_{MEAN}$ and a diastolic blood pressure value $BP_{DIA}$, according to a well known oscillometric blood pressure determining algorithm, based on variation of respective amplitudes of pulses of the pulse wave represented by the pulse wave signal SM1 obtained while the cuff pressure $P_C$ is slowly decreased. At Step SA7, the CPU 29 additionally determines a pulse rate of the subject based on the interval between two successive pulses of the pulse wave signal SM1. The CPU 29 controls the display 32 to display the thus determined blood pressure values and the pulse rate value. Then, the CPU 29 switches the selector valve 16 to its quick-deflation position.

Step SA7 is followed by Step SA8 corresponding to the information storing means 100. At Step SA8, the control device 28 stores, in the predetermined area of the RAM 33, a group of information including the PWP time $DT_{RP}$ last determined at Step SA2, the heartbeat period RR last determined at Step SA3, the VPWA ratio VR last determined at Step SA4, and the systolic BP value $BP_{SYS}$ last determined at Step SA7.

Step SA8 is followed by Step SA9 to judge whether more than four (i.e., not less than five) groups of information have been stored in the RAM 33. If a negative judgment is made at Step SA9, the control goes to Steps SA10 and SA11 to select an appropriate group of predetermined coefficients α, β, γ and determine a constant δ, for the expression (2).

First, at Step SA10, the control device 28 selects, from a plurality of groups of predetermined coefficients (α, β, γ) which correspond to a plurality of blood-pressure ranges, lo respectively, shown in FIG. 5, one group of predetermined coefficients which corresponds to the reference value of the blood pressure of the subject, i.e., the systolic BP value $BP_{SYS}$ measured at Step SA7, so that an estimated systolic blood pressure $EBP_{SYS}$ is successively calculated according to the expression (2) 15 including the selected group of predetermined coefficients. Step SA10 corresponds to the coefficient determining means 82.

Subsequently, the CPU 29 carries out Step SA11 corresponding to the constant determining means 83. At Step SA11, the CPU 29 determines the constant δ of the expression (2), by subtracting, from the systolic BP value $BP_{SYS}$ determined at Step SA7 and used at Step SA8 to select the one group of predetermined coefficients α, β, γ, the sum of the first product of the coefficient α and the inverse of the time $DT_{RP}$ obtained at Step SA2, the second product of the coefficient β and the period RR obtained at Step SA3, and the third product of the coefficient γ and the ratio VR obtained at Step SA4. Assuming that the time $DT_{RP}$, period RR, and ratio VR obtained at Steps SA2, SA3, and SA4 are represented by symbols $DT_{RP0}$, period $RR_0$, and ratio $VR_0$, the constant δ is obtained according to the following expressions (3) and (4):

$$BP_{SYS} = \alpha(1/DT_{RP0}) + \beta RR_0 + \gamma VR_0 + \delta \quad (3)$$

$$\delta = BP_{SYS} - \{\alpha(1/DT_{RP0}) + \beta RR_0 + \gamma VR_0\} \quad (4)$$

On the other hand, if a positive judgment is made at Step SA9, the control goes to Step SA12 corresponding to the relationship (or expression) determining means 102. At Step SA12, the control device 28 determines the coefficients α, β, γ and the constant δ of the expression (2), by applying the multiple regression analysis to more than four, and not more than twenty, groups of information that have been last stored in the RAM 33.

Figure 7:
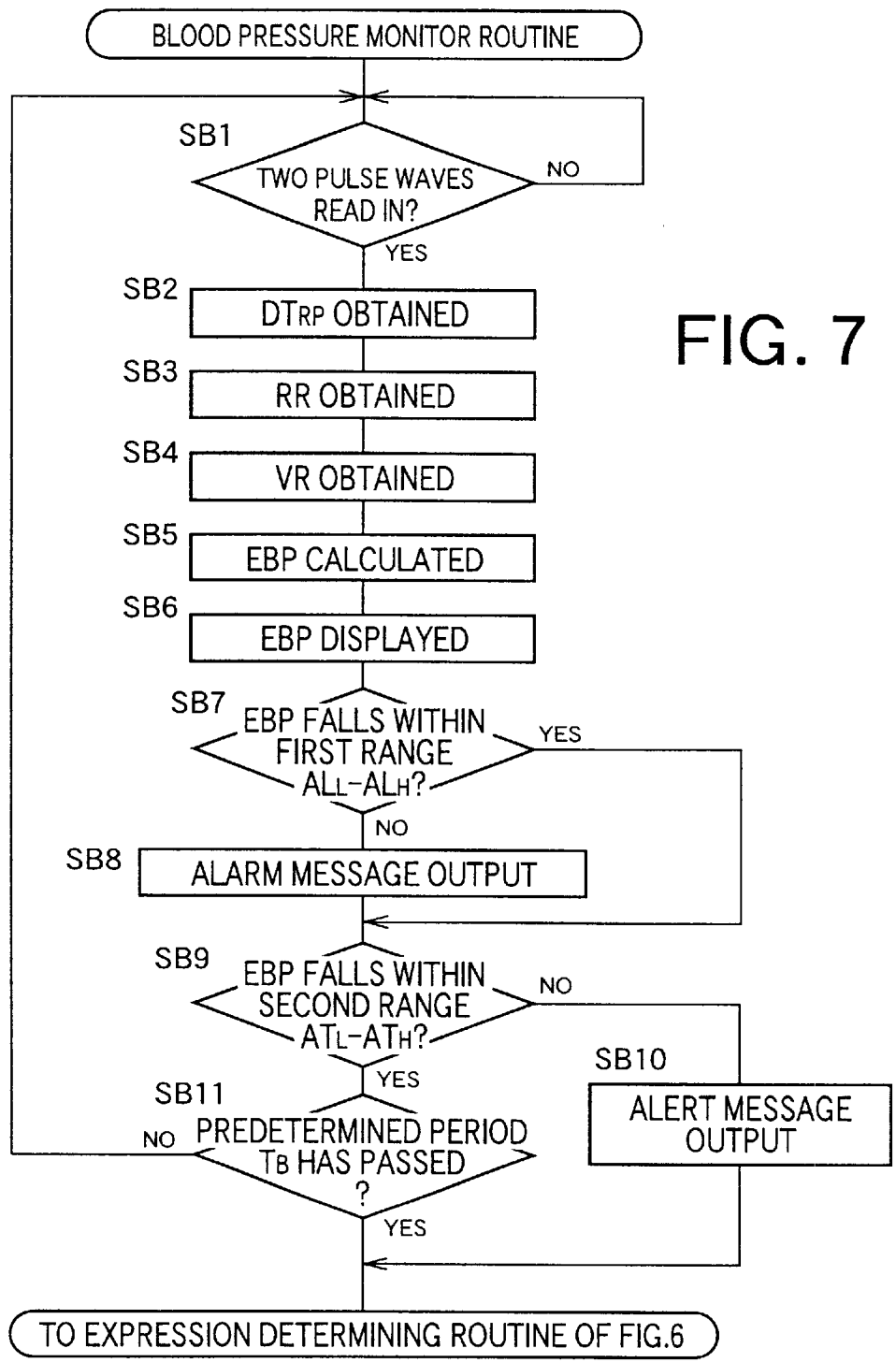
FIG. 7 is a flow chart representing a blood pressure monitoring routine according to which the apparatus of FIG. 1 is operated.

Then, the control of the CPU 29 goes to Step SB1 of the blood pressure monitoring routine of FIG. 7.

At Step SB1, the CPU 29 judges whether or not an R-wave of the ECG waveform of one pulse and a waveform of a corresponding pulse of the photoelectric pulse wave have been read in. If a negative judgment is made at Step SB1, the control of the CPU 29 waits until a positive judgment is made at Step SB1. If a positive judgment is made at Step SB1, the control of the CPU 29 goes to Steps SB2, SB3, and SB4 which are the same as Steps SA2, SA3, and SA4. Step SB2 corresponds to the PWP information obtaining means 70. Step SB3 corresponds to the HR information obtaining means 74. Step SB4 corresponds to the VPWA information obtaining means 76. Thus, the CPU 29 determines a time $DT_{RP}$, a period RR, and a ratio VR at Steps SB2, SB3, and SB4, respectively.

Step SB4 is followed by Step SB5 corresponding to the BP estimating means 80. At Step SB5, the CPU 29 calculates an estimated systolic blood pressure value $EBP_{SYS}$, based on the time $DT_{RP}$, the heart-beat period RR, and the ratio VR obtained at Steps SB2 to SB4, according to the expression (2) including the group of predetermined coefficients α, β, γ selected at Step SA10 and the constant δ determined at Step SA11.

Step SB5 is followed by Step SB6 corresponding to the display means 98. At Step SB6, the CPU 29 operates the display 32 to display, in a two-dimensional coordinate system defined by a first axis indicative of time and a second axis indicative of blood pressure as shown in FIG. 8, estimated systolic blood pressure values $EBP_{SYS}$ successively calculated at Step SB5. The two-dimensional coordinate system is displayed in a predetermined portion of the CRT screen of the display device 32. Moreover, the display 32 displays two first lines $L_{ALH}$, $L_{ALL}$ (indicated at solid lines in FIG. 8) which are indicative of the upper and lower limits of the first reference (alarm) range, respectively, and which are parallel to the first axis, and two second lines $L_{ATH}$, $L_{ATL}$ (indicated at broken lines in FIG. 8) which are indicative of the upper and lower limits of the second reference (alert) range contained in the first reference range, respectively, and which are parallel to the first axis.

Next, at Step SB7, the CPU 29 judges whether or not the estimated blood pressure EBP calculated at Step SB5 falls within a first reference range ($AL_L$–$AL_H$). For example, the CPU 29 judges whether or not the estimated blood pressure EBP is smaller than a lower limit $AL_L$ of the first reference range, and whether or not the estimated blood pressure EBP is greater than an upper limit $AL_H$ of the first reference range. The upper limit $AL_H$ of the first reference range is set at a value which is, by 30%, greater than an initial estimated blood pressure EBP calculated at Step SB5 after the BP measurement using the cuff 10 is carried out at Step SA7 of FIG. 6. The lower limit $AL_L$ of the first reference range is set at a value which is, by 30%, smaller than the initial estimated blood pressure EBP calculated at Step SB5. Step SB7 corresponds to the first judging means 92.

If a positive judgment is made at Step SB7, the control of the CPU 29 goes to Step SB9. On the other hand, if a negative judgment is made at Step SB7, the control of the CPU 29 goes to Step SB8. At Step SB8, the CPU 29 displays, on the display device 32, a visible message (e.g., characters or symbols) indicating that the estimated blood pressure EBP does not fall within the first reference range, and outputs, from the speaker (not shown) of the display 32, an audible message (e.g., alarm sounds or voice sounds) indicating that the estimated blood pressure EBP does not fall within the first reference range. Step SB8 corresponds to the display means 98.

Next, at Step SB9, the CPU 29 judges whether or not the estimated blood pressure EBP calculated at Step SB5 falls within a second reference range ($_{ATL}$–$AT_H$). For example, the CPU 29 judges whether or not the estimated blood pressure EBP is smaller than a lower limit $AT_L$ of the second reference range, and whether or not the estimated blood pressure EBP is greater than a upper limit $AT_H$ of the second reference range. The upper limit $AT_H$ is set at a value which is, by 15 mmHg, smaller than the upper limit $AL_H$ of the first reference range. The lower limit $AT_L$ is set at a value which is, by 15 mmHg, greater than the lower limit $AL_L$ of the first reference range. Step SB9 corresponds to the second judging means 94.

If a negative judgment is made at Step SB9, the control of the CPU 29 goes to Step SB10. At Step SB10, the CPU 29 displays, on the display device 32, a visible message (e.g., characters or symbols) indicating that the estimated blood pressure EBP does not fall within the second reference range, and outputs, from the speaker, an audible message (e.g., alarm sounds or voice sounds) indicating that the estimated blood pressure EBP does not fall within the second reference range. Step SB10 corresponds to the display means 98. Step SB10 is followed by the routine of FIG. 6 to execute the BP measurement with the cuff 10. As shown in FIG. 8, in the present embodiment, the BP measurement with the cuff 10 is executed at a time point $t_{ATH}$. Accordingly, the blood pressure measured using the cuff 10 can be obtained at the time point $t_{ATH}$ earlier than a time point $t_{ALH}$ (shown in FIG. 8) when the BP measurement with the cuff 10 is started based on only the judgment that the estimated blood pressure value EBP does not fall within the first reference range.

If a positive judgment is made at Step SB9, the control of the CPU 29 goes to Step SB11. At Step SB11, the CPU 29 judges whether or not a predetermined calibration period $T_B$ has passed after the last BP measurement using the cuff 10 is carried out at Step SA7 of FIG. 6. The predetermined calibration period $T_B$ is a relatively long time period such as several minutes or several tens of minutes. In the case where the accuracy of the expression (2) is more important than the need to reduce the burden exerted to the patient because of frequent pressing of the cuff 10, the calibration period $T_B$ is predetermined at a short time (e.g., several minutes) so that as many as possible groups of information may be collected in a time duration in which the relationship between the blood pressure BP and the PWP time $DT_{RP}$ is kept constant. On the other hand, in the case where the need to reduce the burden exerted to the patient is more important, the period $T_B$ is predetermined at a long time (e.g., several tens of minutes).

If a negative judgment is made at Step SB11, the control of the CPU 29 returns to Step SB1. If a positive judgment is made at Step SB11, the control of the CPU 29 goes to the routine of FIG. 6 to carry out the oscillometric BP measurement using the cuff 10 and determine the expression (2) at Steps SA8 to SA12.

In the above described embodiment, the BP estimating means 80 (Step SB5) calculates, according to the predetermined relationship (i.e., the expression (2)) between estimated blood pressure EBP, and time $DT_{RP}$, period RR, and ratio VR, the estimated blood pressure value $EBP_{SYS}$ of the subject, based on the obtained time $DT_{RP}$, the obtained period RR, and the obtained ratio VR. Thus, the present apparatus 8 can obtain the estimated blood pressure $EBP_{SYS}$ with high accuracy. In the present embodiment, the estimated blood pressure is estimated based on, in addition to the time $DT_{RP}$, the period RR as the parameter on the side of the heart of the subject that changes in relation with the blood pressure of the subject and the ratio VR as the parameter on the side of the peripheral portion of the subject that changes in relation with the blood pressure of the subject. Thus, it is not needed to frequently calibrate the present apparatus 8 based on the actual blood pressure value BP of the subject measured using the cuff 10, because the estimated blood pressure $EBP_{SYS}$ enjoys higher accuracy in comparison with an estimated blood pressure which is estimated based on only the time $DT_{RP}$ as the first information.

In addition, in the illustrated embodiment, the information storing means 100 (Step SA8) stores, at the predetermined period $T_B$, a group of information comprising the systolic BP value $BP_{SYS}$ measured by the blood-pressure measuring means 96 (Step SA7), the PWP time $DT_{RP}$ obtained by the PWP-information obtaining means 70 (Step SA2) when the systolic BP value $BP_{SYS}$ is measured by the BP measuring means 96, and the heartbeat rate RR and the VPWA ratio VR obtained by the circulation-information obtaining means 72 (Steps SA3, SA4) when the systolic BP value $BP_{SYS}$ is measured by the BP measuring means 96, and the expression determining means 102 determines the coefficients α, β, γ and the constant δ of the expression (2) by applying the multiple regression analysis to more than four groups of information which have been last stored by the information storing means 100. Thus, the expression (2) is determined based on the groups of information which have been last stored in the RAM 33 in the time duration in which the relationship between the systolic BP values $BP_{SYS}$ measured by the BP measuring means 96, and the PWP time values $DT_{RP}$ measured when those BP values $BP_{SYS}$ are measured is kept constant. Therefore, the dispersion included in the groups of information stored in the RAM 33 can be minimized, and the expression (2) or the relationship can be so determined as to be suitable for the individual subject.

In the above embodiment, the coefficients α, β, γ are determined by applying the multiple regression analysis to many groups of information obtained from many persons. Each of the groups of information includes a blood pressure obtained from a corresponding one of the persons, and a time $DT_{RP}$, a period RR, and a ratio VR obtained from the same person when the blood pressure is obtained from the person. Thus, the present apparatus 8 can obtain, even in an early period of operation thereof, a widely applicable relationship or expression (2) for successively calculating an estimated blood pressure value EBP of the subject.

While the present invention has been described in its preferred embodiment by reference to the drawings, it is to be understood that the invention may otherwise be embodied.

For example, in the illustrated embodiment the expression (2) used by the BP estimating means 80 (Step SB5) for calculating the estimated blood pressure EBP employs both of the heart-beat period RR as the heart-rate information and the volume-pulse-wave area ratio VR as the volume-pulse-wave-area information, it is possible to employ only one of the period RR and the ratio VR.

In the illustrated embodiment, the expression (2) for calculating the estimated blood pressure EBP is a liner expression. However, the expression (2) may be a quadratic or higher-order expression. Moreover, the expression (2) may include a trigonal function or logarithm function. For example, the following expression (5) or (6) may be employed in place of the expression (2):

$$EBP=\alpha(1/DT_{RP})+\gamma VR^2+\delta \quad (5)$$

where α and γ are coefficients and δ is a constant.

$$EBP=\alpha(1/DTRP)+\beta\log(RR)+\gamma VR+\delta \quad (6)$$

where α, β, and γ and are coefficients and δ is a constant.

In the illustrated embodiment, every estimated blood pressure EBP is calculated according to only the single expression (2). However, an estimated blood pressure EBP may be calculated according one of a plurality of different expressions which corresponds to a reference blood pressure of the subject. The one expression is selected from the different expressions which respectively correspond to a plurality of blood-pressure ranges, in the same manner as the manner in which one group of coefficients is selected for the single expression (2).

In the illustrated embodiment, at Step SA10 corresponding to the coefficient determining means 82, the three coefficients α, β, γ are determined based on a reference blood pressure of the subject. However, only one or two of the three coefficients which influences or influence the estimated blood pressure EBP may be selected based on the reference blood pressure, and the others or other may be constant values or value, because the influence of each coefficient on the estimated blood pressure EBP may change depending on the blood-pressure ranges.

In the illustrated embodiment, the time $DT_{RP}$ is calculated based on the time difference between the R-wave of the ECG waveform and the minimum point of the waveform of the photoelectric pulse wave. However, the time $DT_{RP}$ may be calculated based on a time difference between a Q-wave of the ECG waveform of each pulse and the minimum point of the waveform of a corresponding pulse of the photoelectric pulse wave.

In the illustrated embodiment, an estimated blood pressure EBP is determined based on the R-wave of the ECG waveform of each heartbeat-synchronous pulse and the waveform of a corresponding pulse of the photoelectric pulse wave. However, an estimated blood pressure EBP may be determined based on every second, third, or so on pulse of the ECG waveform and every second, third, or so on pulse of the photoelectric pulse wave.

It is to be understood that the present invention may be embodied with other changes and modifications that may occur to those skilled in the art without departing from the scope of the invention.

What is claimed is:

1. An apparatus for successively estimating an intraarterial blood pressure of a living subject, based on information non-invasively obtained from a circulatory organ of the subject, comprising:

a blood-pressure measuring device which includes an inflatable cuff adapted to apply a pressing force to a body portion of the subject and iteratively measures, by changing the pressing force of the cuff, a blood pressure of the subject at a predetermined period;

a first means for non-invasively obtaining, from the circulatory organ of the subject, a set of first information which relates to a velocity of propagation of a pulse wave which propagates through an artery of the subject, at least each time the blood-pressure measuring device measures a blood pressure of the subject;

a second means for non-invasively obtaining, from the circulatory organ of the subject, at least one of a set of second information which relates to a heart rate of the subject and a set of third information which relates to an area defined by a volume pulse wave from a peripheral portion of the subject, at least each time the blood-pressure measuring device measures said blood pressure;

a first memory device which stores a plurality of groups of information each group of which comprises said blood pressure measured by the blood-pressure measuring device, the set of first information obtained by the first means when said blood pressure is measured by the blood-pressure measuring device, and said at least one of the set of second information and the set of third information obtained by the second means when said blood pressure is measured by the blood-pressure measuring device;

an expression determining means for determining an expression representing a relationship between (A) blood pressure, and (B1) first information and (B2) at least one of (B21) second information and (B22) third information, the expression having a first coefficient for the first information, at least one second coefficient for said at least one of the second information and the third information, and a constant, the expression determining means determining the first and second coefficients and the constant of the expression by applying a multiple regression analysis to more than a first predetermined number of said groups of information last stored in the first memory device, the first predetermined number being equal to a total number of the first coefficient, said at least one second coefficient, and the constant; and a blood-pressure estimating means for successively estimating, according to the determined expression representing the relationship between (A) blood pressure, and (B1) first information and (B2) at least one of (B21) second information and (B22) third information, an intraarterial blood pressure of the subject, based on each of a plurality of sets of first information successively obtained by the first means and at least one of each of a plurality of sets of second information, and each of a plurality of sets of third information, successively obtained by the second means when said each of sets of first information is obtained by the first means.

2. An apparatus according to claim 1, wherein the expression determining means comprises means for determining the first and second coefficients and the constant of the expression by applying the multiple regression analysis to not more than a second predetermined number of said groups of information last stored in the first memory device, the second predetermined number being greater than the first predetermined number.

3. An apparatus according to claim 1, wherein the second means obtains the set of second information and the set of third information, and wherein the blood-pressure estimating means comprises means for estimating, according to the expression representing the relationship between (A) blood pressure, and (B1) first information, (B21) second information, and (B22) third information, the intraarterial blood pressure of the subject, based on said each set of first information obtained by the first means, and each set of second information and each set of third information obtained by the second means when said each set of first information is obtained by the first means.

4. An apparatus according to claim 3, wherein the first means comprises means for obtaining, as the set of first information, a time, DT, which is needed for the pulse wave to propagate between two different portions of the artery, wherein the second means comprises means for obtaining, as the set of second information, a heart-beat period, RR, of the subject, and means for obtaining, as the set of third information, a ratio, VR, of the area of the volume pulse wave to the heart-beat period RR, and wherein the blood-pressure estimating means comprises means for successively estimating, according to the expression representing the relationship between (A) blood pressure, EBP, and (B1) time DT, (B21) period RR, and (B22) ratio VR, defined as follows: $EBP = \alpha(1/DT) + \beta RR + \gamma VR + \delta$, where $\alpha$ is the first coefficient, $\beta$ and $\gamma$ are the second coefficients, and $\delta$ is the constant, an intraarterial blood pressure of the subject, based on each of a plurality of values of the time DT successively obtained by the first means, and each of a plurality of values of the period RR, and each of a plurality of values of the ratio VR, successively obtained by the second means when said each value of the time DT is obtained by the first means.

5. An apparatus according to claim 4, further comprising a second memory device which stores at least one group of predetermined first and second coefficients $\alpha$, $\beta$, $\gamma$ of the expression that are predetermined by applying the multiple regression analysis to a plurality of groups of information which are obtained from a plurality of persons and each group of which comprises a blood pressure obtained from a corresponding one of the persons, and a time DT, a period RR, and a ratio VR which are obtained from said one person when said blood pressure is obtained from said one person, wherein, before the first memory device stores more than said first predetermined number of groups of information, the blood-pressure estimating means successively estimates, according to the expression having said one group of predetermined first and second coefficients $\alpha$, $\beta$, $\gamma$, an intraarterial blood pressure of the subject, based on each of a plurality of values of the time DT successively obtained by the first means and each of a plurality of values of the period RR, and each of a plurality of values of the ratio VR, successively obtained by the second means when said each value of the time DT is obtained by the first means.

6. An apparatus according to claim 1, wherein the second means comprises means for obtaining the set of third information selected from the group consisting of the area defined by the volume pulse wave, a ratio of the area to a heart-beat period of the subject, a ratio of the area to a product of the heart-beat period and an amplitude of the volume pulse wave, and a ratio of a product of the area and the amplitude to the heart-beat period.

7. An apparatus according to claim 1, wherein the first means comprises:
   a first pulse-wave sensor and a second pulse-wave sensor which non-invasively detect the pulse wave from two different portions of the artery of the subject, respectively; and
   means for determining, as the set of first information, a time which is needed for the pulse wave to propagate between the two different portions of the artery.

8. An apparatus according to claim 7, wherein the second means comprises means for determining, as the set of second information, a time difference between respective predetermined points of two successive heartbeat-synchronous pulses of the pulse wave detected by one of the first and second pulse-wave sensors.

9. An apparatus according to claim 7, wherein the second means comprises one of the first and second pulse-wave sensors, said one pulse-wave sensor detecting the volume pulse wave from the peripheral portion of the subject.

10. An apparatus according to claim 7, wherein the first and second pulse-wave sensors comprise an electrocardiograph and a photoelectric oximeter.

11. An apparatus for successively estimating an intraarterial blood pressure of a living subject, based on information non-invasively obtained from a circulatory organ of the subject, comprising:
   a blood-pressure measuring device which includes an inflatable cuff adapted to apply a pressing force to a body portion of the subject and iteratively measures, by changing the pressing force of the cuff, a blood pressure of the subject;
   a first means for non-invasively obtaining, from the circulatory organ of the subject, a set of first information which relates to a velocity of propagation of a pulse wave which propagates through an artery of the subject, at least each time the blood-pressure measuring device measures a blood pressure of the subject;
   a second means for non-invasively obtaining, from the circulatory organ of the subject, at least one of a set of second information which relates to a heart rate of the subject and a set of third information which relates to an area defined by a volume pulse wave from a peripheral portion of the subject, at least each time the blood-pressure measuring device measures said blood pressure;
   a memory device which stores a plurality of groups of information each group of which comprises said blood pressure measured by the blood-pressure measuring device, the set of first information obtained by the first means when said blood pressure is measured by the blood-pressure measuring device, and said at least one of the set of second information and the set of third information obtained by the second means when said blood pressure is measured by the blood-pressure measuring device;

an expression determining means for determining an expression representing a relationship between (A) blood pressure, and (B1) first information and (B2) at least one of (B21) second information and (B22) third information, the expression having a first coefficient for the first information, at least one second coefficient for said at least one of the second information and the third information, and a constant, the expression determining means determining the first and second coefficients and the constant of the expression, based on more than a predetermined number of said groups of information last stored in the memory device, the predetermined number being equal to a total number of the first coefficient, said at least one second coefficient, and the constant; and a blood-pressure estimating means for successively estimating, according to the determined expression representing the relationship between (A) blood pressure, and (B1) first information and (B2) at least one of (B21) second information and (B22) third information, an intraarterial blood pressure of the subject, based on each of a plurality of sets of first information successively obtained by the first means and each of a plurality of sets of said at least one of the second information and the third information successively obtained by the second means when said each set of first information is obtained by the first means.

12. An apparatus according to claim 11, wherein the expression determining means comprises means for determining the first and second coefficients and the constant of the expression, by applying a statistic analysis to more than said predetermined number of groups of information last stored in the memory device.

13. An apparatus according to claim 11, wherein the expression determining means comprises means for determining the first and second coefficients and the constant of the expression, by applying a multiple regression analysis to more than said predetermined number of groups of information last stored in the memory device.

* * * * *